US00PP10478P

United States Patent [19]

Harkness

[11] Patent Number: Plant 10,478

[45] Date of Patent: Jul. 7, 1998

[54] FLORIBUNDA ROSE PLANT NAMED 'HARFLOW'

[75] Inventor: Robert Harkness, Mougins, France

[73] Assignee: Weeks Wholesale Rose Grower, Inc., Upland, Calif.

[21] Appl. No.: 735,235

[22] Filed: Oct. 22, 1996

[51] Int. Cl.[6] ..... A01H 5/00

[52] U.S. Cl. ..... Plt./22

[58] Field of Search ..... Plt./22, 24

[56] References Cited

U.S. PATENT DOCUMENTS

P.P. 4,520 4/1980 Paolino ..... Plt./22

P.P. 5,582 12/1985 Harkness ..... Plt./22

P.P. 9,161 6/1995 Harkness ..... Plt./22

OTHER PUBLICATIONS

Upourom, 1997/03, Plant Variety Database, Retrieval Software GTI Jouve, 'Harflow' citation.

*Primary Examiner*—Howard J. Locker

*Attorney, Agent, or Firm*—Christie, Parker & Hale, LLP

[57] ABSTRACT

A new plant variety of Floribunda rose suitable for garden decoration, having flowers of yellow gold coloration.

1 Drawing Sheet

BACKGROUND OF THE INVENTION

This invention relates to a new and distinct variety of Floribunda Rose. The varietal denomination of the new variety is 'Harflow'. The plant is a bushy upright plant, suitable for outdoor garden decoration. It was discovered as a naturally occurring mutation of the cultivar 'Harwelcome' (U.S. Plant Pat. No. 9,161).

SUMMARY OF THE INVENTION

Among the features which distinguish the new variety from other presently available and known commercial rose cultivars are the following combination of characteristics: its golden yellow flowers with good color stability for this color group, its glossy bright green foliage, its light colored young prickles, and its unusually high degree of resistance to blackspot. 'Harflow' may be asexually propagated by cuttings, budding, and grafting.

Asexual reproduction of the new variety by budding as performed in Kern County and Upland, Calif. shows that the foregoing and other distinguishing characteristics come true to form and are established and transmitted through succeeding propagations.

Comparison with Parents

The new rose may be distinguished from its parent, 'Harwelcome' by the following combination of characteristics: whereas 'Harwelcome' produces flowers of a blended orange coloration, 'Harflow' produces flowers of a golden yellow coloration. The parent has glossy green foliage often suffused with red pigment, whereas the new variety has significantly lighter green foliage with no suffusion of darker pigmentation. The prickles of the branches and new shoots of 'Harwelcome' are of a darker coloration than the prickles on the branches and new shoots of 'Harflow'.

BRIEF DESCRIPTION OF ILLUSTRATION

The accompanying photograph illustrates flowers and foliage of the new variety, showing the flowering thereof from bud to full bloom, depicted in color as nearly correct as it is possible to make in a color illustration of the character. To illustrate comparison with the parent, the photo shows a bloom of the parent on the right having a contrasting reddish coloration. Throughout the description herein, color values are based upon The Colour Chart of The Royal Horticultural Society of London, England, except where common terms of color definition are employed.

DESCRIPTION OF THE NEW VARIETY

The following description is of rose plants of the new cultivar grown outdoors in Upland, Calif. in the month of August. Phenotypic expression may vary with environmental, cultural and climatic conditions, as well as differences in conditions of light and soil. The following description is directed to the description of characteristics of the new variety that are different than the parent. In respect of characteristics not disclosed, the description is substantially the same as the parent (as described in U.S. Plant Pat. No. 9,161) the description in which is hereby expressly incorporated herein as reference.

Bud

As the first petals open, the color of the under surfaces of the newly opened petals is between 12B and 14C at the petal base suffusing slowly toward the top of the petal to between 16A and 24C. At the very top of the petal under surface, the color is sometimes blushed with between 29B and 35B. The color of the upper surfaces of the newly opened petals is between 12A and 14B at the petal base suffusing toward the top of the petal to between 15C and 24B. At the middle and uppermost portion of the petal upper surface, the color is sometimes irregularly washed with coloration as deep as between 35A and 29B.

The peduncle is of short to average length for the class, of average caliper, and usually erect. It is almost entirely smooth with some stipitate glands and hairs. Peduncle color is between 138A and 144A, sometimes lightly blushed on the side facing the sun with near 178C. The peduncle length is short to average, about 3 to 5 cm. The green bud is moderately small, about 1.5 to 2 cm at the widest point and about 2.5 to 3 cm in length. The opening bud is about 2 to 2.5 cm at the widest point and about 2.5 to 3 cm in length.

Before the calyx breaks, the bud is of moderately small size for the class, medium in length, and pointed to ovoid in shape. The surface of the bud bears some stipitate glands and fine hairs, with slender foliaceous parts extending beyond the tip of the bud equal to ¼ or more of its length. Bud color is between 138A and 144A.

The new variety bears its flowers sometimes singly, usually three to four or more per stem. Flowers are borne in regular flat to rounded clusters on strong medium to long stems for the class. Outdoors the plant blooms very abundantly and nearly continuously during the growing season. The flowers have a slight fruity fragrance. Stem length is medium to long, generally about 25 to 42 cm. The inner surface of the sepals is covered with fine wooly tomentum; sepal margins are lined with many stipitate glands and hairs.

As the first petal opens, the bud is somewhat small to medium size for the class, medium in length, and somewhat pointed to ovoid in form.

Newly Opened Flower

The under surface of the outer, intermediate and inner petals is between 14C and 12B at the petal base, suffusing slowly toward the top of the petal to between 16A and 24C. The upper surface of the outer, intermediate and inner petals is between 12A and 14B at the petal base, suffusing toward the top of the petal to between 15C and 24B. At the middle and uppermost portion of the petal upper surface, the color is sometimes washed with as deep as between 33D and 29B.

The general tonality of the newly opened flower is between 15C and 24B.

When fully open, the bloom is medium sized for the class, ranging from 9 to 10.5 cm. in diameter. Petalage is double with 25 to 30 petals and 1 and 5 petaloids arranged regularly. When partially open, the bloom form is somewhat cupped and the petals are somewhat undulated. When fully open, the bloom form is somewhat more flat to cupped and the petals are moderately loosely undulated to reflexed backward.

The petals are of moderately heavy substance and of medium thickness, with inside surfaces slightly velvety and outside slightly satiny. The outer petals are very broadly obovate in shape with a mostly rounded apex. The intermediate petals are somewhat obovate to nearly round in shape with the apex usually rounded to flat. The inner petals are more narrowly obovate in shape.

Three Day Old Flower

The under surface of the outer, intermediate and inner petals is between 14C and 12B at the petal base, suffusing slowly toward the top of the petal to between 16C and 23C. The upper surface of the outer, intermediate and inner petals is between 12B and 14C at the petal base, suffusing toward the top of the petal to between 16B and 23C. There is no wash of color at the middle and uppermost portion of the petal upper surface.

The general tonality of the three day old flower is between 16B and 23C.

On the spent bloom, the petals usually drop off cleanly and are not particularly affected by cold, hot, wet or dry weather.

In August, bloom on the bush growing in the garden generally last from three to four or more days. Cut roses grown outdoor and kept at normal indoor living temperatures generally last from four to five or more days.

Foliage

The upper surface of the mature leaf is between 139B and 146A. The under surface of the mature leaf is between 139C and 194A. The upper surface of the young leaf is between 137C and 144A, with no suffusion of darker pigmentation. The under surface of the young leaf is between 138B and 147C.

The compound leaves are usually comprised of three to five and sometimes seven leaflets and are borne abundantly. The leaves are of moderate size for the class, very heavy to leathery in texture, and very glossy in finish. The leaflets are shaped moderately ovate to ovoid with somewhat acute apices and somewhat round bases. Their margins are usually doubly serrate. Leaflets are about 3.5 to about 7 cm in length and about 2 to about 4.5 in width at the widest point. Leaves are about 9 to 13 cm in length and about 7 to 9 cm in width at the widest point.

The rachis is average in caliper and moderately rough to grooved with some hairs and stipitat glands on the edges of the upper side. The underside of the rachis is moderately rough with some stipitate glands and few prickles.

The stipules are of medium width, short to medium length, and have straight points that usually turn out at an angle of less than 90 degrees.

The plant displays a very high degree of resistance to blackspot and an above average degree of resistance to powdery mildew and rust as compared to other commercial varieties grown under comparable conditions in Upland, Calif.

The plant has a bushy upright medium height habit with very full branching. It displays very vigorous growth and the canes are of medium to heavy caliper for the class. The plant achieves a medium height of about 105 to 130 cm and a width of about 90 to 115 cm.

The color of the major stems is near 146B. They bear several large prickles which are moderately long for the class. The large prickles are almost straight with a somewhat short narrow base: prickle color is near 177A. The major stem bears many small prickles of similar shape and coloration.

The branches bear several large prickles which are moderately long for the class. The large prickles are almost straight with a somewhat short narrow base; prickle color is near 160B. The branches bear several small prickles of similar shape and coloration and some coarse hairs.

The new shoots bear several large prickles which are moderately long for the class. The large prickles are almost straight with a somewhat short narrow base, prickle color is near 144B. The new shoots also bear many small prickles of similar shape and coloration and many coarse hairs.

Growth

The prickle color of the branches is near 160B.

The prickle color of the new shoots is near 144B

Male Reproduction Organs

Stamens are average to many in number and are arranged regularly about the pistil. The filaments are of irregular medium to long length, most with anthers. The anthers are moderately small for the class and all open approximately at the same time. Anther color is near 26A when immature and near 172A at maturity. Pollen is moderate to abundant and near 15C in color.

Female Reproduction Organs

Pistils are moderately abundant in number (approximately 90). The styles are somewhat uneven, moderately short in length, average in caliper, and moderately bunched. Stigma color is near 10D. Style color is near 42C. Ovaries are usually all enclosed in the calyx.

Hips are somewhat short in length, very globular in form, and become near 30C in color when mature. The hip surface is very smooth with somewhat thick fleshy walls. The sepals fall away soon after seed set. Seeds are moderately few in number (approximately 8 to 13), and average in size.

I claim:

1. A new and distinct variety of rose plant of the Floribunda rose class, substantially as described and illustrated herein.

* * * * *

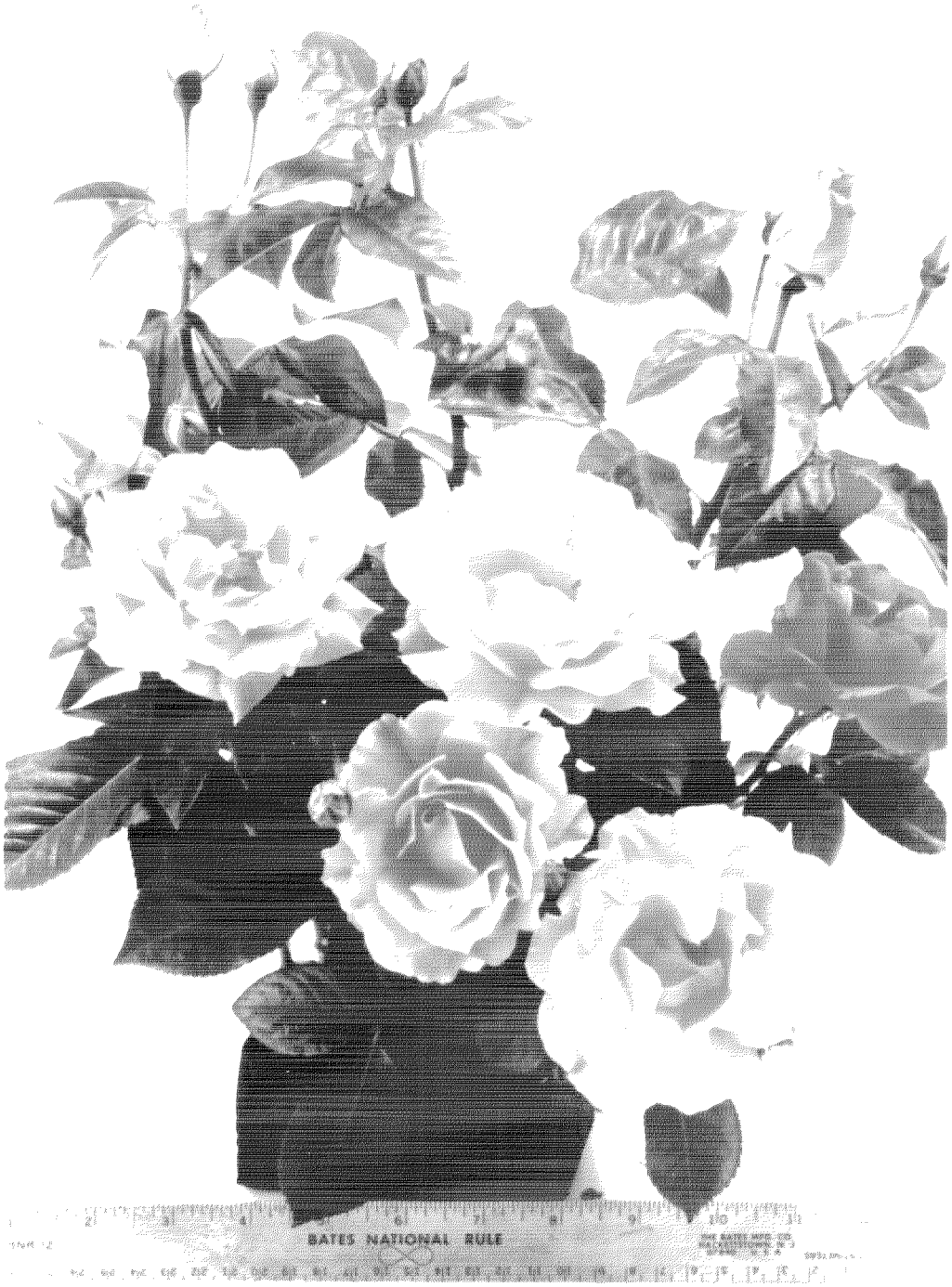
BATES NATIONAL RULE

UNITED STATES PATENT AND TRADEMARK OFFICE

CERTIFICATE OF CORRECTION

PATENT NO. : Plant 10,478
DATED : July 7, 1998
INVENTOR(S) : Robert Harkness

It is certified that error appears in the above-indentified patent and that said Letters Patent is hereby corrected as shown below:

Column 3, line 34, change "1 and 5" to -- 1 to 5 --.
Column 3, line 64, change "outdoor" to -- outdoors --.
Column 4, line 20, change "stipitat" to -- stipitate --.

Column 4, line 54, delete "The prickle color of the branches is near 160B.".
Column 4, line 56, delete "The prickle color of the new shoots is near 144B".

Signed and Sealed this
Thirtieth Day of November, 1999

*Attest:*

*Attesting Officer*

Q. TODD DICKINSON

*Acting Commissioner of Patents and Trademarks*